United States Patent
Wheeler

[19]

[11] Patent Number: 6,120,509
[45] Date of Patent: Sep. 19, 2000

[54] INTRAMEDULLARY REFERENCE DATUM INSTRUMENT

[75] Inventor: John L. Wheeler, Round Rock, Tex.

[73] Assignee: Sulzer Orthopedics Inc., Austin, Tex.

[21] Appl. No.: 09/145,363

[22] Filed: Sep. 1, 1998

[51] Int. Cl.[7] .................................................. A61F 5/00
[52] U.S. Cl. ................... 606/87; 606/88; 623/20
[58] Field of Search .................. 606/87, 88, 80; 623/20

[56] References Cited

U.S. PATENT DOCUMENTS

| | | | |
|---|---|---|---|
| 5,258,032 | 11/1993 | Bertin ........................................ | 623/20 |
| 5,397,360 | 3/1995 | Cohen et al. ............................. | 623/20 |
| 5,411,505 | 5/1995 | Mumme .................................... | 606/88 |
| 5,464,406 | 11/1995 | Ritter et al. ............................... | 606/68 |
| 5,665,090 | 9/1997 | Rockwood et al. ...................... | 606/87 |

FOREIGN PATENT DOCUMENTS

| | | |
|---|---|---|
| 0 556 998 A1 | 8/1993 | European Pat. Off. . |
| 0 714 645 A1 | 6/1996 | European Pat. Off. . |
| 0 919 195 A1 | 2/1999 | European Pat. Off. . |

*Primary Examiner*—Michael Buiz
*Assistant Examiner*—Julian W. Woo
*Attorney, Agent, or Firm*—Philip S. Lyren; Kenneth S. Barrow

[57] ABSTRACT

An intramedullary reference instrument is provided for aligning a cutting instrument in connection with surgical implantation of an orthopedic prosthesis having a stem component. The intramedullary reference instrument includes a stem trial having a length and diameter corresponding to that of the stem component of the prosthesis, and also includes a first connector. The instrument further includes a shaft adapter having a first end portion including a second connector. The second connector is configured for mating with the first connector of the stem trial to removably connect the shaft adapter to the stem trial. The shaft adapter is engageable with the cutting instrument to properly align the cutting instrument.

13 Claims, 2 Drawing Sheets

FIG. 3
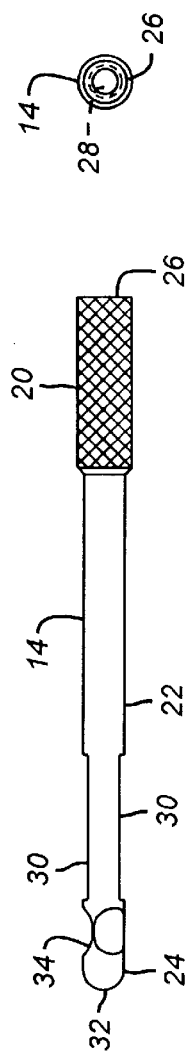
FIG. 2
FIG. 4
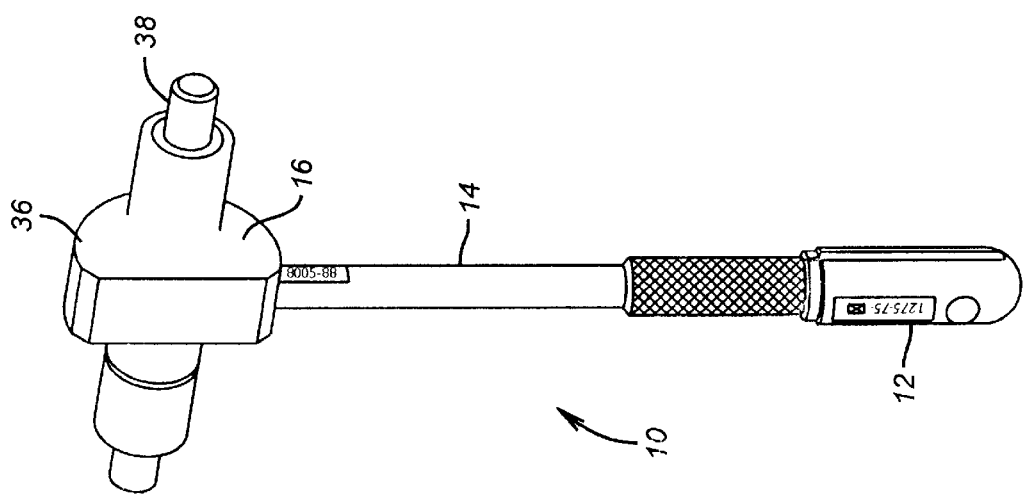
FIG. 1

INTRAMEDULLARY REFERENCE DATUM INSTRUMENT

BACKGROUND OF THE INVENTION

1. Field of the Invention

The present invention relates generally to implantable orthopedic prostheses for replacing human skeletal joints, and surgical instruments for implanting such prostheses, and relates more particularly to surgical instruments for preparing human bones to receive implantable orthopedic prostheses.

2. Background of the Related Art

Implantable orthopedic prostheses, in one form, comprise man-made replacements for the ends and articulating surfaces of the bones of the skeleton. Such prostheses are implanted to repair or reconstruct all or part of an articulating skeletal joint that is functioning abnormally due to disease, trauma, or congenital defect. Among the various articulating skeletal joints of the human body that are eligible to be fitted with implantable orthopedic prostheses, the hip, knee and shoulder joints are most often treated with such prostheses. The performance of each of these joints has an important effect on quality of life. The hip and knee joints play a critical role in ambulation and the shoulder joint plays a critical role in manual dexterity, resulting in great demand for surgical correction of abnormalities of these joints.

As used herein, the words proximal and distal are terms of reference that indicate a particular portion of a bone or prosthesis component according to the relative disposition of the natural bone or implanted prosthesis. Proximal indicates that portion of a component nearest the torso, whereas distal indicates that portion of a component farthest from the torso. Directional terms of reference used herein include superior, inferior, anterior, posterior, medial and lateral, which are used according to their commonly understood anatomical meanings. More particularly, with regard to a person in a standing position, superior means upward, inferior means downward, anterior means forward, posterior means rearward, medial means inwardly from the side toward the center of the body, and lateral means outwardly from the center of the body toward the side.

The human knee joint involves three bones: the femur, the tibia and the patella, each having a smooth articulation surface arranged for articulation against an adjacent articulation surface of one or more of the other bones. The femur includes at its distal extremity two spaced, generally convex condyles, comprising a medial and a lateral condyle, having an intercondylar groove therebetween extending generally in the anterior-posterior direction. The anterior end of the intercondylar groove extends up the anterior face of the distal femur to form a shallow patellar groove. The tibia includes at its proximal extremity a tibial platform comprising two spaced, generally convex meniscal surfaces disposed in opposition to the medial and lateral condyles of the distal femur, and forming articulating surfaces against which the condylar articulating surfaces of the distal femur articulate. The patella, attached via the patellar tendon to the tibia and femur, has a generally convex posterior articulating surface that articulates against the patellar groove of the anterior distal femur.

As a result of disease, congenital defect, or trauma, one or more of the articulating surfaces of the bones comprising the knee joint may fail to function properly. In that event, surgical intervention is sometimes necessary to restore function. One such surgical intervention involves implanting a total knee prosthesis, in which at least the tibial and femoral articulating surfaces are replaced with prosthetic articulating surfaces. Often, the posterior articulating surface of the patella is also replaced with a prosthetic articulating surface. In such surgery, the ends of the affected bones of the knee joint are resected to provide a stabile bony surface of predetermined geometry against which the prosthetic articulating surfaces can be secured. The placement of the resection cuts is critically important to insure that after the prosthetic components are implanted, the stability of the knee, as controlled by soft-tissue, and the kinematics of the knee will be restored to an anatomically correct condition. It is customary, therefore, to provide specialized instrumentation to assist the surgeon in properly locating all resections of the bones of the knee joint, with the instrumentation being specially configured for the prosthesis that is to be implanted.

To help assure that the femoral and tibial components of the prosthetic knee are properly aligned and spaced to restore the knee joint to an anatomically correct condition, it is useful to provide a common reference datum for controlling the location of the resections of the distal femur and proximal tibial. One known method for providing a reference datum is to temporarily fix an instrument in the medullary canal of either the femur or the tibia for supporting or positioning other instruments, such as cutting blocks, to guide the resection cuts. It is known to place a bullet-shaped reamer in the medullary canal to provide such a reference datum. Another known technique includes placing an intramedullary rod in the medullary canal and using adapter sleeves positioned around the rod, which aid in aligning the cutting instruments. Also known is the technique of assembling a stem trial directly to the cutting instrument.

Certain disadvantages of the prior techniques discussed above have been noted. Bullet reamers will sometimes snake down the medullary canal, resulting in a false representation of the canal center, and therefore, misguided cuts. Bullet reamers typically have a short cutting section at the end, followed by a shank of reduced diameter. Such reamers provide only a limited length of engagement with the medullary canal. Because of the short engagement length, the reamer can be unstable as a reference datum. The use of adapter sleeves in conjunction with an intramedullary rod requires a different sleeve for each size of stem. Using an intramedullary rod alone foregoes the benefit of using a stem trial that is appropriately sized to fit the canal that has been reamed to receive a particular stem size. Assembling the stem trial directly to the cutting block requires multiple assembly steps when the surgical technique requires changing cutting blocks. In order to change cutting blocks, the stem trial and attached cutting block must both be removed from the patient, then disconnected from one another, then the stem trial must be reattached to the new cutting block.

Accordingly, it would be desirable to provide an intramedullary reference datum that is stabile and that enhances the accuracy and reproducibility of the resection cuts required for implanting an orthopedic prosthesis. The present invention, a particular embodiment of which is shown and described below, provides these and other desirable advantages.

SUMMARY OF THE INVENTION

It is an object of the invention to provide an intramedullary reference instrument for aligning a cutting instrument in connection with the implantation of orthopedic prostheses.

It is a further object of the present invention to provide an intramedullary reference instrument for aligning a cutting instrument in connection with surgical implantation of an orthopedic prosthesis having a stem component. The intramedullary reference instrument comprises a stem trial having a length and diameter corresponding to that of the stem component of the prosthesis, and a first connector. The instrument further comprises a shaft adapter having a first end portion including a second connector, the second connector configured for mating with the first connector of the stem trial to removably connect the shaft adapter to the stem trial. The shaft adapter is engageable with the cutting instrument to properly align the cutting instrument.

It is yet another object of the present invention to provide an intramedullary reference instrument for aligning a cutting instrument in connection with surgical implantation of orthopedic prostheses of varying sizes each having a stem component. The instrument comprises a plurality of stem trials having varying lengths and diameters corresponding to those of the stem components of the prostheses of varying sizes, and including a first connector. The intramedullary reference instrument further comprises a shaft adapter having a first end portion including a second connector. The second connector is configured for mating with any of the first connectors of the stem trials to removably connect the shaft adapter to any of the stem trials, and the shaft adapter is engageable with the cutting instrument to properly align the cutting instrument.

It is yet another object of the present invention to provide a method for aligning a cutting instrument used in connection with surgical implantation of an orthopedic prosthesis having a stem component. The method comprises the steps of forming a cavity in the medullar canal of a bone of a patient to receive the orthopedic prosthesis, connecting a stem trial having a length and diameter corresponding to that of the stem component of the orthopedic prosthesis to a shaft adapter by engaging a first connector of the stem trial with a second connector of the shaft adapter which is located at a first end portion of the shaft adapter, inserting the connected stem trial and adapter shaft into the cavity in the medullary canal, and engaging the cutting instrument with the shaft adapter to properly align the cutting instrument.

Other objects and advantages of the present invention will be apparent to one skilled in the pertinent art from the following descriptions of a preferred embodiment made with reference to the drawings.

BRIEF DESCRIPTION OF THE DRAWINGS

FIG. 1 is a perspective view of an intramedullary reference instrument according to the present invention, and a handle used in conjunction with such an instrument.

FIG. 2 is a side view of an adapter component of the instrument of FIG. 1.

FIG. 3 is an end view of the adapter component of FIG. 2.

FIG. 4 is a side view of a stem trial component of the instrument of FIG. 1.

DETAILED DESCRIPTION OF THE PREFERRED EMBODIMENT

Figure 5:
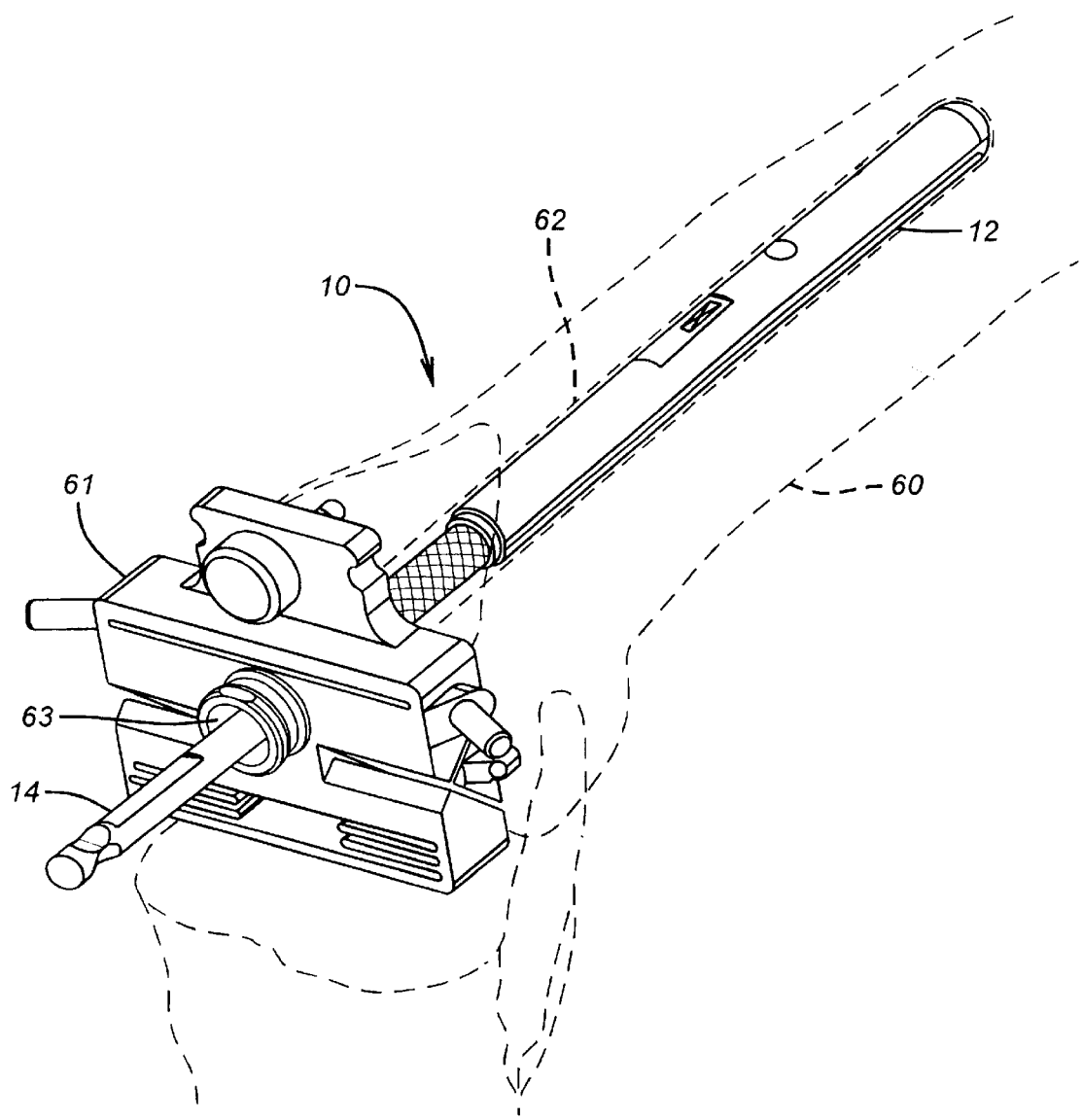
FIG. 5 illustrates the instrument of FIG. 1 inserted within a bone and aligning a cutting instrument.

Referring particularly to FIGS. 1–4, a preferred embodiment of the present invention is illustrated in the form of an intramedullary reference instrument 10 having two principle components: a stem trial 12 and an adapter shaft 14. A handle 16, also shown in FIG. 1, which engages to the adapter shaft 14, may be used to assist the user in inserting and removing the intramedullary reference instrument from a patient.

Stem trial 12 replicates, with respect to length and diameter, the medullary stem of the implantable prosthesis. Stem trial 12 is designed for temporary implantation during the course of surgery, for trial fitting purposes, but is not designed for permanent implantation. It is common to use trial components during surgery to confirm the accuracy of reaming and resection operations. The use of a trial component for test purposes preserves the sterility of the implantable component and protects the implantable component from damage that might be incurred during the repeated handling and extraction that takes place during trial fittings. Stem trial 12 is provided in a range of lengths and diameters corresponding to the lengths and diameters of the various sizes of stems associated with the implantable prostheses, which prostheses are provided in a range of sizes to fit different patients. Stem trial 12 is designed for modular assembly to a trial prosthesis, and therefore is provided with an externally threaded male shank 18 extending axially from the proximal end of stem trial 12. To promote modular interchangeability, threaded shank 18 is provided in a common length, diameter and thread pitch, independent of the length and diameter of the stem trial 12.

Shaft adapter 14 includes a first end portion 20, an intermediate portion 22, and a second end portion 24. First end portion 20 is generally cylindrical, knurled on the external surface, and includes an end face 26 in which an internally threaded axial bore 28 is provided. Axial bore 28 is constructed in the same length, diameter and thread pitch of threaded shank 18 of stem trial 12 to permit threaded shank 18 to be threadably received within axial bore 28. Stem trial 12 and shaft adapter 14 are removably connectable to each other by way of threaded shank 18 and threaded bore 28. Since the shaft adapter is connectable with any size stem trial, the combination stem trial and adapter provides an improved intramedullary reference instrument, as will be described below.

Knurled first end portion 20 of adapter shaft 14 is provided in a length that corresponds to the common length of the stem boss of the femoral prosthesis to which the stem prosthesis attaches. By design, the length of the knurled first end portion also corresponds to the common length of the keel boss of the tibial prosthesis baseplate. Consequently, with stem trial 12 and shaft adapter 14 connected together and inserted within the reamed medullary canal of either the femur or tibia, first end portion 20 is located in the same relative position that the stem boss or keel boss of the implantable component will occupy, in relation to the lateral-medial and anterior-posterior directions. In addition, the first end portion 20, when so inserted, provides an axial datum in relation to the superior-inferior direction. Intermediate portion 22 comprises a generally cylindrical shaft, coaxial with first end portion 20, and having a constant diameter of 5/16 inch, as preferred. A pair of diametrically opposed flats 30 are recessed within intermediate portion 22 at that end of intermediate portion 22 away from first end portion 20 and closest to second end portion 24. Flats 30 provide a location for part numbers and other markings to be etched without disturbing the outer cylindrical surface of intermediate portion 14 that serves as the reference datum, or reference point from which a cutting instrument can be aligned. Second end portion 24 is generally cylindrical and has a like diameter as intermediate portion 22, and is provided with a hemispherical end 32. In a preferred embodiment, second end portion 24 also includes three scalloped recesses 34 equally spaced about the circumference of second end portion 24, with the adjacent scalloped recesses just touching each other. Each scalloped recess 34 is substantially cylindrical in curvature with an axis transverse to the length of shaft adapter 14. A handle 16 may be provided which includes a main body 36 and a transverse lock shaft 38 slidingly disposed within main body 36 for reciprocating sliding displacement transversely to the length of shaft adapter 14. When the handle 36 is connected to shaft adapter 14, lock shaft 38 engages one of the three scalloped recesses 34 to lock handle 36 to shaft adapter 14.

FIG. 5 illustrates the intramedullary reference instrument 10 in position within a human bone 60, such as the femur, and used to align a cutting block 61 used to resect the bone. As can be seen, the combination stem trial 12 and adapter shaft 14 provides a stable reference for positioning cutting block 61. Not only is the novel intramedullary reference instrument 10 stabile in that it is firmly positioned (will not wobble etc.) within the medullary canal, but the combination stem trial and shaft adapter closely mimics the portion of the prosthesis that will sit within the medullary canal, further ensuring that the required bone resections will be properly aligned relative to this part of the actual implant.

The intramedullary reference instrument 10 described above may be used in an improved method for aligning a cutting instrument in connection with surgical implantation of an orthopedic prosthesis. A cavity 62 is first formed in the medullary canal of a bone 60 of a patient, such as the tibia, that is to receive a portion of an implantable prosthesis. The cavity may be formed by reaming out a portion of the medullary canal in a manner that is well known in the art. The stem trial 12 is then connected to the shaft adapter 14 by securing the threaded shank 18 of the stem trial with the threaded bore 28 of the shaft adapter. The connected stem trial and shaft adapter is then inserted into the cavity formed in the medullary canal, and once inserted, the cutting instrument 61 is engaged with the adapter shaft to properly align the cutting instrument. As shown in FIG. 5, the cutting instrument 61 may have a hole 63 through it, and the cutting instrument is engaged with the shaft adapter by sliding the hole 63 of cutting block 61 over the intermediate portion 22 of the shaft adapter so that the intermediate portion is used to properly align the cutting instrument 61.

While the present invention has been described in terms of a preferred embodiment with particular reference to the drawings, it should be understood that the description is merely exemplary and that the scope of the subject matter that is regarded as the invention is limited only by the appended claims.

What is claimed is:

1. An intramedullary reference instrument for aligning a cutting instrument in connection with surgical implantation of an orthopedic prosthesis having a stem component, comprising:

a stem trial having a length and diameter corresponding to that of the stem component of said prosthesis, said stem trial including a first connector;

a shaft adapter having a first end portion including a second connector, and a second end having a third connector, said second connector configured for mating with said first connector of said stem trial to removably connect said shaft adapter to said stem trial, said shaft adapter further includes an elongate shaft adjacent said first end portion, said elongate shaft being engageable with said cutting instrument to property align said cutting instrument; and a handle having a fourth connector for releasably engaging said third connector of said shaft adapter to removably attach said handle to said shaft adapter.

2. An intramedullary reference instrument according to claim 1, wherein said elongate shaft has an intermediate portion that is substantially cylindrical.

3. An intramedullary reference instrument accordingly to claim 2, wherein said first end portion of said shaft adapter is substantially cylindrical and has a knurled outer surface, said first end portion having a diameter greater than that of said intermediate portion.

4. An intramedullary reference instrument according to claim 1, wherein said prosthesis includes a stem mounting boss, and said first end portion of said shaft adapter has a length corresponding to that of said stem mounting boss.

5. An intramedullary reference instrument according to claim 1, wherein said elongate shaft has an intermediate portion that is substantially cylindrical.

6. An intramedullary reference instrument according to claim 5, wherein said first end portion of said shaft adapter is substantially cylindrical and has a knurled outer surface, said first end portion having a diameter greater than that of said intermediate portion.

7. An intramedullary reference instrument for aligning a cutting instrument in connection with surgical implantation of orthopedic prostheses of varying sizes each having a stem component, comprising:

a plurality of stem trials having varying lengths and diameters corresponding to those of the stem components of said prostheses of varying sizes, said stem trial including a first connector;

a shaft adapter having a first end portion including a second connector, and a second end portion including a third connector, said second connector configured for mating with any of said first connectors of said stem trials to removably connect said shaft adapter to any of said stem trials, said shaft adapter being engageable with said cutting instrument to properly align said cutting instrument; and a handle having a fourth connector for releasably engaging said third connector of said of said shaft adapter to removably attach said handle to said shaft adapter.

8. An intramedullary reference instrument according to claim 7, wherein said shaft adapter further includes an elongate shaft adjacent said first end portion, said elongate shaft being engageable with said cutting instrument to properly align said cutting instrument.

9. An intramedullary reference instrument according to claim 8, wherein said elongate shaft has an intermediate portion that is substantially cylindrical.

10. The intramedullary reference instrument according to claim 9, wherein said first end portion of said shaft adapter is substantially cylindrical and has a knurled outer surface, said first end portion having a diameter greater than that of said intermediate portion.

11. An intramedullary reference instrument according to claim 10, wherein said prosthesis includes a stem mounting boss, and said first end portion of said shaft adapter has a length corresponding to that of said stem mounting boss.

12. A method for aligning a cutting instrument in connection with surgical implantation of an orthopedic prosthesis having a stem component, comprising the steps of:

forming a cavity in the medullar canal of a bone of a patient to receive said orthopedic prosthesis;

connecting a stem trial having a length and diameter corresponding to that of said stem component of said orthopedic prosthesis to a shaft adapter by engaging a first connector of said stem trial with a second connector of said shaft adapter located at a first end portion of said shaft adapter, wherein said shaft adapter further includes an elongate shaft having an intermediate portion adjacent said first end portion that is substantially cylindrical, said intermediate portion of said elongate shaft being engageable with said cutting instrument to properly align said cutting instrument, said first end portion having a diameter greater than that of said intermediate portion;

inserting said connected stem trial and adapter shaft into said cavity in said medullary canal; and engaging said cutting instrument with the shaft adapter to properly align said cutting instrument.

13. The method according to claim 12, wherein said prothesis includes a stem mounting boss, and said first end portion of said shaft adapter has a length corresponding to that of said stem mounting boss.

* * * * *